(12) United States Patent
Essenpreis et al.

(10) Patent No.: US 11,350,821 B2
(45) Date of Patent: Jun. 7, 2022

(54) AMBULATORY MEDICAL DEVICE AND METHOD FOR COMMUNICATION BETWEEN MEDICAL DEVICES

(75) Inventors: Matthias Essenpreis, Burgdorf (CH); Ulrich Haueter, Grosshoechstetten (CH); Nicole Bernini, Ersigen (CH); Sybille Fankhauser, Zollikofen (CH); Sebastiaan La Bastide, Muri bei Bern (CH); Gunnar Meyer Olden, Burgdorf (CH); Michael Schoemaker, Mannheim (DE); Kelly Heaton, Ersigen (CH); Joel Jeckelmann, Villars-sur-Glane (CH)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 1088 days.

(21) Appl. No.: 11/832,421

(22) Filed: Aug. 1, 2007

(65) Prior Publication Data

US 2008/0033255 A1 Feb. 7, 2008

Related U.S. Application Data

(63) Continuation of application No. PCT/EP2006/000663, filed on Jan. 26, 2006.

(30) Foreign Application Priority Data

Feb. 2, 2005 (EP) .................................... 05002074

(51) Int. Cl.
*A61B 5/00* (2006.01)
*A61M 5/142* (2006.01)
*A61B 5/145* (2006.01)

(52) U.S. Cl.
CPC ....... *A61B 5/0002* (2013.01); *A61M 5/14244* (2013.01); *A61B 5/14532* (2013.01);
(Continued)

(58) Field of Classification Search
CPC .............. A61B 5/0002; A61B 5/14532; A61B 5/14277; A61M 5/14244; A61M 5/14276;
(Continued)

(56) References Cited

U.S. PATENT DOCUMENTS 5,507,288 A * 4/1996 Bocker et al. ................ 600/322
6,290,646 B1 * 9/2001 Cosentino et al. ........... 600/300
(Continued)

FOREIGN PATENT DOCUMENTS

EP 0 098 592 1/1984

*Primary Examiner* — Rex R Holmes
*Assistant Examiner* — Sana Sahand
(74) *Attorney, Agent, or Firm* — Woodard, Emhardt, Henry, Reeves & Wagner, LLP

(57) ABSTRACT

An ambulatory medical device and a method of communication between medical devices are disclosed. In one embodiment, the medical device includes a module for communication with at least a second medical device wherein the module for communication is adapted to be activated by a value of a physiological parameter of an animal. In one embodiment, the method of the present invention involves a first medical device and at least a second medical device wherein the communication between said medical devices is activated by a value of a physiological parameter of an animal.

15 Claims, 2 Drawing Sheets

(52) U.S. Cl.
CPC . *A61M 5/14276* (2013.01); *A61M 2205/3523* (2013.01); *A61M 2205/3569* (2013.01); *A61M 2205/3592* (2013.01); *A61M 2230/201* (2013.01)

(58) Field of Classification Search
CPC .. A61M 2205/3523; A61M 2205/3569; A61M 2205/3592; A61M 2230/201
USPC .......................................................... 600/300
See application file for complete search history.

(56) References Cited

U.S. PATENT DOCUMENTS

| | | | |
|---|---|---|---|
| 6,295,506 B1* | 9/2001 | Heinonen et al. ............ | 702/104 |
| 6,553,244 B2* | 4/2003 | Lesho et al. .................. | 600/347 |
| 6,572,543 B1* | 6/2003 | Christopherson et al. ... | 600/300 |
| 6,641,533 B2* | 11/2003 | Causey et al. ................. | 600/300 |
| 6,659,948 B2* | 12/2003 | Lebel ................ | A61N 1/37211 |
| | | | 600/300 |
| 7,034,677 B2* | 4/2006 | Steinthal et al. ........ | 340/539.12 |
| 7,276,029 B2* | 10/2007 | Goode et al. ................. | 600/365 |
| 7,278,983 B2* | 10/2007 | Ireland et al. .................. | 604/66 |
| 2002/0010390 A1* | 1/2002 | Guice et al. .................. | 600/300 |
| 2002/0016568 A1* | 2/2002 | Lebel .................... | A61M 5/172 |
| | | | 604/131 |
| 2002/0049389 A1 | 4/2002 | Abreu | |
| 2002/0143241 A1* | 10/2002 | Thorell ........................ | 600/300 |
| 2002/0151770 A1* | 10/2002 | Noll et al. .................... | 600/300 |
| 2003/0041866 A1* | 3/2003 | Linberg ............... | A61B 5/0031 |
| | | | 128/899 |
| 2003/0065536 A1* | 4/2003 | Hansen et al. ................ | 600/300 |
| 2003/0114898 A1* | 6/2003 | Von Arx ................ | A61N 1/08 |
| | | | 607/60 |
| 2003/0136418 A1* | 7/2003 | Behm .................... | G16H 40/67 |
| | | | 128/899 |
| 2004/0077995 A1* | 4/2004 | Ferek-Petric ........... | A61M 5/14 |
| | | | 604/66 |
| 2004/0102971 A1* | 5/2004 | Lipscher et al. ............. | 704/236 |
| 2004/0116786 A1* | 6/2004 | Iijima et al. ................... | 600/301 |
| 2004/0122702 A1* | 6/2004 | Sabol et al. ....................... | 705/2 |
| 2004/0167464 A1 | 8/2004 | Ireland et al. | |
| 2004/0225338 A1 | 11/2004 | Lebel et al. | |
| 2005/0080322 A1* | 4/2005 | Korman ........................ | 600/300 |
| 2005/0113717 A1* | 5/2005 | Matzinger et al. ........... | 600/573 |
| 2005/0182306 A1* | 8/2005 | Sloan ...................... | H04B 7/24 |
| | | | 600/300 |
| 2005/0192557 A1* | 9/2005 | Brauker et al. ............... | 604/503 |
| 2005/0195930 A1* | 9/2005 | Spital .................. | A61M 5/14244 |
| | | | 375/368 |
| 2007/0282177 A1* | 12/2007 | Pilz .............................. | 600/301 |
| 2010/0179409 A1* | 7/2010 | Kamath ............. | A61B 5/14865 |
| | | | 600/365 |

* cited by examiner

AMBULATORY MEDICAL DEVICE AND METHOD FOR COMMUNICATION BETWEEN MEDICAL DEVICES

CROSS-REFERENCE TO RELATED APPLICATION(S)

This application is a continuation of International Application No. PCT/EP2006/000663, filed on Jan. 26, 2006, which claims priority to European Patent Application No. 05 002 074.2, filed on Feb. 2, 2005, the contents of both of which are incorporated in their entirety herein by reference.

BACKGROUND

The present invention relates devices for injecting, infusing, delivering, dispensing or administering substances, and to methods of making and using such devices. More particularly, it relates to an ambulatory medical device and a method of communication for or communicating between or among medical devices.

Ambulatory medical devices include devices for the treatment of diabetes, e.g. extra corporal insulin pumps and blood glucose measuring devices such as hand held glucose meters. Insulin pumps allow a good control of blood glucose concentrations by continuously infusing a basic amount of insulin in a human body (basal insulin rate) and by allowing manually controlled delivery of additional "meal bolus" insulin quantities thereby reflecting the insulin secretion by the pancreas. Furthermore, the development of continuous glucose sensors will allow measuring in vivo glucose concentrations over the whole day. The measured glucose date can be used to adjust the diabetes therapy to individual needs.

To improve the treatment of medical conditions, including diabetes, it would be helpful to provide a way to transfer data and/or communicate information between and/or among medical devices in a way that assures optimal quality and accuracy of the function of the devices, the information being communicated, and the exchange of the information.

SUMMARY

It is an object of the present invention to provide a medical system and method providing a controlled data transfer between medical devices.

In one embodiment, the present invention comprises a medical device comprising a module for communication with at least a second medical device wherein the module for communication in the medical device is adapted to be activated by a value of a physiological parameter of an animal.

In one embodiment, the medical device and/or devices comprise a telemetry system or feature for wireless communication, e.g. in one preferred embodiment, a telemetry system for RF communication.

In some preferred embodiments, the medical device is selected from the group consisting of a remote control, a PDA, an analyte measuring device, e.g., a glucose measuring device such as a hand held glucose meter, a strip based or strip type glucose meter, or combinations thereof.

In some embodiments, the physiological parameter may be selected from the group consisting of an analyte concentration, a physiological characteristic like conductivity of an animal, a physiological vital sign such as heart or breath rate, temperature, movement, air- or structure-borne sound, ECG (electrocardiogram), etc. In one preferred embodiment of the present invention, the analyte concentration is a blood glucose concentration.

In some preferred embodiments, the medical device of the present invention comprises an electrochemical or photometric module for measuring blood glucose. Suitable medical devices are include strip based glucose meters such as the meter known as the AccuChek Compact.

In one embodiment, the present invention relates to and/or comprises a system of medical devices. The system comprises a first medical device of the present invention as described above and at least a second medical device capable of communicating with the first medical device.

In one preferred embodiment, the second medical device may be selected from the group consisting of an extra corporal infusion pump, an implantable infusion pump, a pacesetter, an analyte or vital sign sensor, a continuous analyte or vital sign sensor, and a continuous glucose sensor.

In another preferred embodiment, the first medical device and the at least second medical device comprise a telemetry system for wireless communication, in some preferred embodiments, a telemetry system for RF communication.

In another aspect, the present invention relates to or comprises a method of communication between a first medical device and at least a second medical device wherein the communication between said medical devices is enabled and/or activated by a value of a physiological parameter of an animal. In a preferred embodiment, the communication between the at least two medical devices is enabled and/or activated for a predetermined time. The time duration can be fixed, random, dependent on the physiological parameter enabling and/or activating the communication, or dependent on other physiological parameters of the animal body.

In some preferred embodiments, the physiological parameter may be selected from the group consisting of an analyte concentration, a physiological characteristic like conductivity of an animal, a physiological vital sign like heart or breath rate, temperature, movement, air- or structure-borne sound, ECG (electrocardiogram), etc. In some preferred embodiments, the analyte concentration is a blood glucose concentration.

In one preferred embodiment, the activation of communication between the medical devices is performed on the first medical device by a value of the physiological parameter.

In some preferred embodiments, the first medical device may be selected from the group consisting of a remote control, a PDA, an analyte measuring device, a glucose measuring device, and a strip based glucose meter. The second medical device may be selected from the group consisting of an extra corporal infusion pump, an implantable infusion pump, a pacesetter, an analyte sensor, a continuous analyte sensor, and a continuous glucose sensor.

In one preferred embodiment, the communication between the medical devices is a wireless communication, e.g., a RF communication. In other preferred embodiments, other suitable forms or methods of communicating information, sensed parameters, data, commands, etc. may be used.

In one preferred embodiment, the first medical device receives data or information from the second medical device, and in another preferred embodiment, the first medical device sends commands to the second medical device controlling at least partially the function or operation of the second medical device.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electronics associated with the invention, if any. Suitable electrical components and circuitry, wires, wireless components, chips, boards, microprocessors, receivers, transmitters, inputs, outputs, displays, control components, etc. may be used. Generally, unless otherwise indicated, the materials used in the invention and/or its components may be selected from appropriate materials such as metal, metallic alloys, ceramics, plastics, etc.

In one aspect, the present invention relates to a method for controlling and/or enabling communication between medical devices, such as medical sensory devices such as continuous glucose sensors and/or therapeutic devices such as insulin pumps and/or diagnostic medical devices such as glucose meters.

Figure 1:
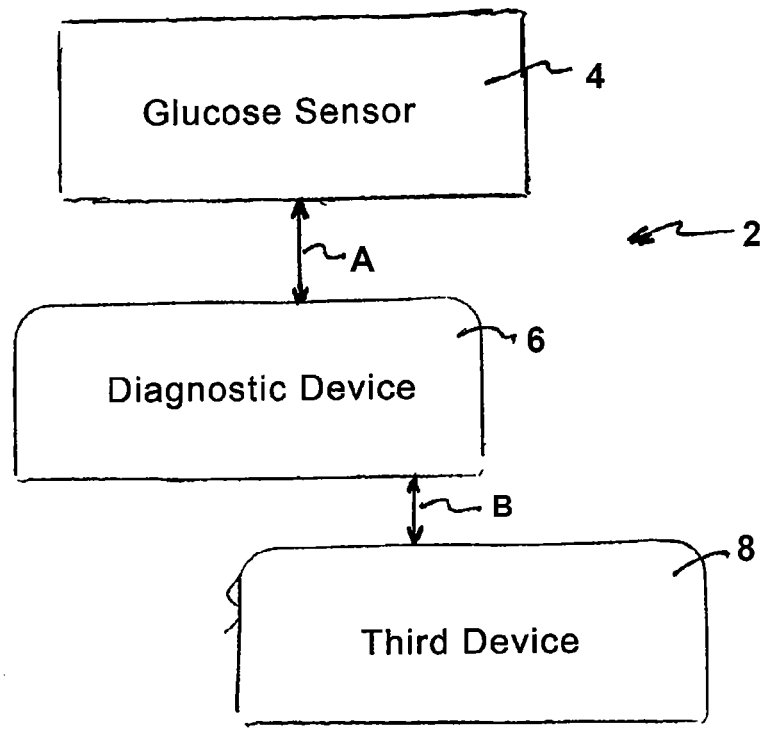
FIG. 1 depicts one exemplary embodiment of the present invention, including arrows depicting the communication and/or flow of information to and from components.

For example, referring to FIG. 1, in one exemplary system 2 in accordance with the present invention, the communication between a continuous glucose sensor 4 applied to a human body and a blood glucose meter 6 can only be established when a blood glucose measurement has been made in the blood glucose meter 6. The generation of the blood glucose value in the blood glucose meter 6 enables and/or activates communication, represented at arrow A, between the two devices for a specified time limit. During the time window data can be transferred from the sensor 4 to the glucose meter 6 and/or commands from the glucose meter 6 can be sent to the sensor 4. After expiration of a time limit, communication between the two devices is deactivated. To establish a further or subsequent communication, the communication link between the two devices has to be activated by generating a further blood glucose value in the glucose meter 6.

The term "generation of a value" as it is used herein encompasses any method or procedure for the determination of physiological parameters such as methods for the measurement of analyte values, e.g., blood glucose values. Suitable methods for the determination of blood glucose values include electrochemical methods, photometric methods and others which are known to a person skilled in the art.

The dependence of the communication link between medical devices on an actual analyte value ensures the quality of the data transmitted from the medical sensory device and/or medical therapeutical device to the medical diagnostic device.

The data transferred from the sensor 4 to the diagnostic device, e.g., the meter 6, can be stored on the diagnostic device and be transferred, as represented by arrow B to a third device 8 such as a PDA or a computer, for further processing and/or analysis. The data can be analyzed and/or processed by suitable software and used, for example, for bolus recommendation or adjustment of basal insulin rates for patients using an extra- or intra corporal insulin pump. The communication link between the diagnostic device 6 and a third device 8 does not necessarily need activation by generation of a blood glucose value in the diagnostic device 6.

Figure 2:
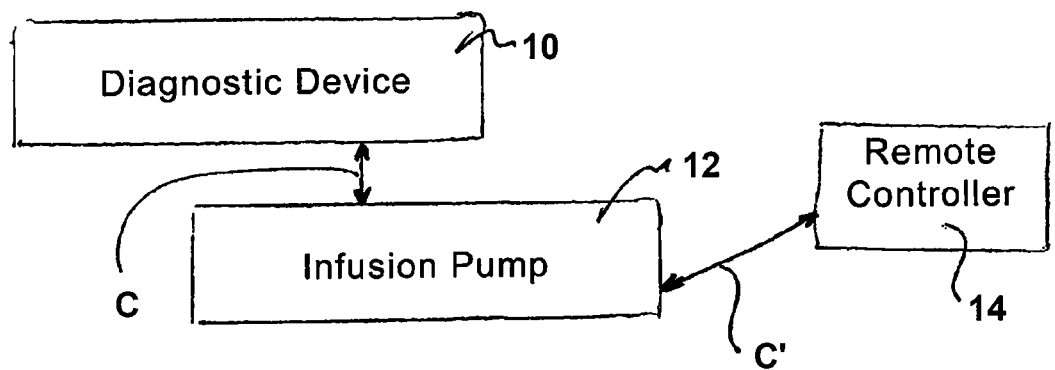
FIG. 2 depicts another exemplary embodiment of the present invention, including arrows depicting the flow of information to and from components.

Referring to FIG. 2, in one preferred embodiment, the present invention relates to a method of communication between a diagnostic medical device 10, e.g., a blood glucose meter, and an infusion pump 12, e.g., an extra corporal insulin pump. In this embodiment, the diagnostic medical device 10 is used as or functions as a remote control to control the function of the infusion pump 12. After a blood glucose value has been generated in the blood glucose meter 10 a communication link, represented by arrow C, between meter 10 and pump 12 is enabled and/or activated for a defined time and commands can be transferred from the remote control, i.e. the glucose meter, to the pump 12. It is also possible to transfer data stored on the pump 12 to the diagnostic device 10 during the communication time window.

With further reference to FIG. 2, in some embodiments comprising a remote controller 14 for the infusion pump 12, the remote controller 14 may not comprise a feature or device for measuring blood glucose concentration. In such embodiments, the communication, represented by arrow C', between pump 12 and remote control 14 is activated by entering a current blood glucose value measured in a blood glucose meter in the remote control 14. The value may be entered using inputs of the remote control 14 or can be transferred via a wireless or wired connection to the glucose meter 10. After the blood glucose value has been entered in the remote control 14, a communication link between remote control 14 and infusion pump 12 is established, preferably for a predetermined time span. After expiration of the time span, the communication is interrupted and no data exchange between the two devices is anymore possible. A further round of communication needs a new activation of the communication by entering a new, current blood glucose value in the remote control 14. The term remote control or controller as used herein encompasses PDA's, smart phones, pump specific remote controllers, etc.

The data transfer between the medical devices can be performed using known and/or available technologies, and may comprise wired and/or wireless components, connections and/or communications. These technologies are known to a person skilled in the art. In one preferred embodiment, communication may be provided RF communication. In some embodiments, the data transfer between the devices can be encrypted to ensure that non-authorized third parties do not gain access to personal data of patients. Any suitable method of encrypting data, including those known to a person skilled in the art, may be used. In some preferred embodiments, the communication between the medical devices may be activated by a manipulation of or on the second medical device, e.g. insulin pump 12, such as pressing a button or lever, inserting a battery, using the touch screen, shaking, bumping or squeezing or the like.

Figure 3:
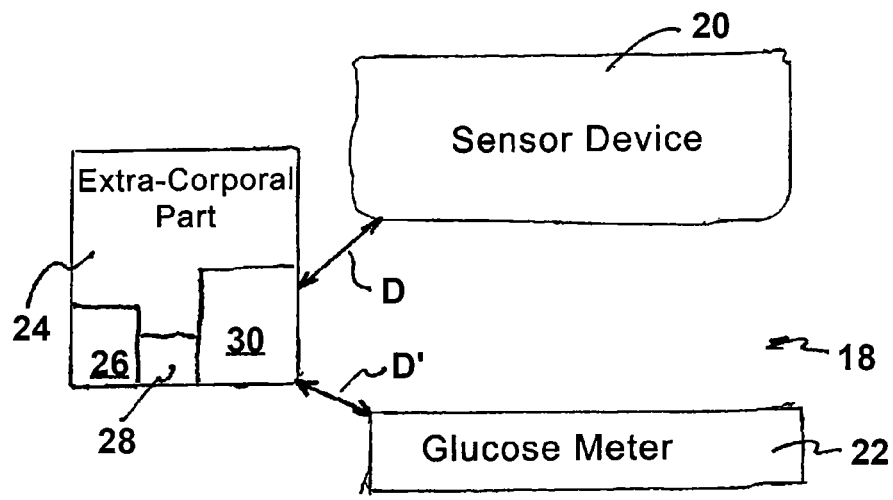
FIG. 3 depicts another exemplary embodiment in accordance with the present invention, including arrows depicting the communication among components.

Referring to FIG. 3, in one preferred embodiment, the present invention comprises a system 18 of medical devices comprising a continuous glucose sensor device 20 which is placed on a human body to measure glucose value in interstitial fluid and a glucose meter 22. The sensor device 20 comprises an electrochemical glucose sensor measuring the glucose concentration in the interstitial tissue in a predetermined manner. The sensor device 20 further comprises an extra-corporal part 24 including a suitable processor or computer 26 for controlling the sensor 20, a suitable memory 28 for storing measured glucose values and a telemetry system or module 30 for transmitting the data to the glucose meter 22, e.g., a strip-based glucose meter. The glucose values stored on the sensor device 20 may then transferred to a glucose meter 22 via the telemetry system 30 (as represented by arrows D and D').

The communication between the devices, i.e. the wireless link, is established and/or activated by measuring the glucose concentration in a blood sample of a patient using the glucose meter 22. When a strip-based glucose meter is used, the patient inserts a strip in the glucose meter and puts a droplet of blood on the strip. The glucose meter 22 measures and indicates the blood glucose value, e.g., on an associated display. After measurement of the blood glucose value, the communication link can then be activated/established either by, for example, pressing an input on the glucose meter 22, e.g. an activation button, or by a direct electronic link to the processor 26 controlling the glucose telemetry system 30 such that the completion of the blood glucose measurement automatically activates the wireless link between the devices.

The communication link is then established and a data transfer between the medical devices is possible and/or occurs for a defined time span. After expiration of the defined time span the communication link is deactivated and no further data/commands can be transmitted between the medical devices. A new blood glucose measurement in the glucose meter 22 is then necessary to open a new wireless link between the medical devices.

In a further aspect, the present invention relates to a method of data processing or data use, wherein the data processing or data use is only possible and/or only occurs after activation by a value of a physiological parameter. The method is may be used for the processing of medical data such as data measured by a sensor applied on a human body.

Figure 4:
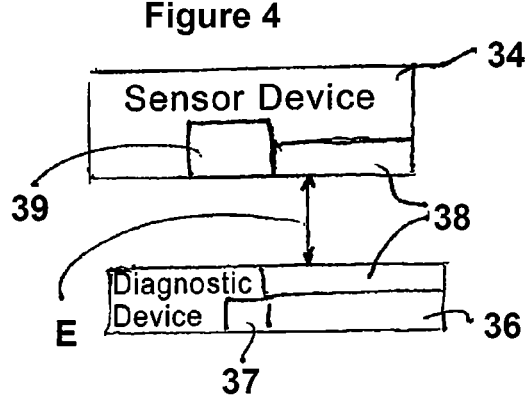
FIG. 4 depicts another exemplary embodiment of the present invention, including arrows depicting the flow of information to and from components.

Referring to FIG. 4, in one preferred embodiment, the method in accordance with the present invention may be used for the processing of medical data sensed or measured by a sensor device 34 applied on a human being, e.g., a continuous glucose sensor. The data is then transferred, as shown by arrow E, to a diagnostic medical device 36, e.g., a blood glucose meter. The data may be transferred via a wireless link from the sensor device 34 to the diagnostic device 36. In this case, each of the at least two medical devices comprises a telemetry system 38 for wireless communication. The wireless communication can be bidirectional or unidirectional.

In some preferred embodiments, there is a permanent communication link between said two medical devices, but the data stored in a memory 39 of the medical sensor device 34 and transferred to the diagnostic device 36 can only be further processed on the diagnostic device 36 after the processing has been activated by a value of a physiological parameter. After activation by a value of a physiological parameter, preferably a blood glucose value, the data stored in the memory 39 of the diagnostic device 36 can be processed or used. For example, data are transferred from a continuous glucose sensor 34 to a glucose meter 36 and stored in the memory of the glucose meter. The further processing of these data is then only possible after activation of the processing by a value of a physiological parameter, e.g., a blood glucose value. In one preferred embodiment, the processing of the data is only possible for a limited time span after activation by a value of a physiological parameter. When the defined time span for data processing has lapsed, no further data processing is possible without a new activation by a value of a physiological parameter.

Figure 5:
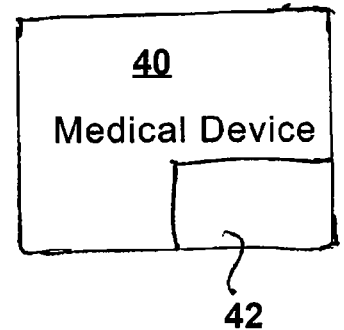
FIG. 5 depicts an exemplary embodiment of a component in accordance with the present invention.

Referring to FIG. 5, in a further aspect the present invention may comprise a medical device 40 comprising a module, feature or component 42 for data processing which is adapted to be activated by a value of a physiological parameter. The module 42 comprises a suitable microprocessor or computer with a memory for storing data. In some preferred embodiments, the medical device 40 is a blood glucose meter. The processing of data stored in the memory of the blood glucose meter 40 may be activated either by pressing an input associated with the glucose meter 40 (e.g., an activation button or switch) or by a direct electronic link to the hardware, firmware and/or software of the data processing module 42 such that the completion of the blood glucose measurement automatically activates data processing. The terms "data processing" or "data use" as they are used herein refer to any manipulation of data and comprise analysis of data, presentation of data, communication of date, interpretation of data, indication of data, etc.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:
1. A system of medical devices comprising:
a glucose measuring device configured to generate a blood glucose value based upon a physiological parameter representative of the blood glucose concentration of an animal; and
a continuous glucose sensor,
said glucose measuring device including a communication module configured to establish a wireless communication link enabling communication between said glucose measuring device and said continuous glucose sensor, the communication module further being configured, in response to completion of the generation of the blood glucose value, to determine a defined length of a time span for the communication link to be established,
the defined length of the time span being determined using a value of the physiological parameter of the animal obtained by said glucose measuring device from said continuous glucose sensor during a previous communication between said glucose measuring device and said continuous glucose sensor;
the communication module further being configured, following determination of the time span, to automatically activate for the defined time span from a deactivated state the wireless communication link,
the communication module of the glucose measuring device being configured that after expiration of the defined time span the communication link between the glucose measuring device and the continuous glucose sensor is deactivated, said glucose measuring device being configured to send information to said continuous glucose sensor during the defined time span, and said continuous glucose sensor being configured to process the information received from said glucose measuring device.

2. The system of claim 1 in which said continuous glucose sensor is configured to process the information during the defined time span.

3. The system of claim 1 in which the communication module is configured to automatically deactivate the communication link upon expiration of the predetermined defined time span.

4. The system of claim 1 in which the value of the physiological parameter of the animal is the blood glucose value of the animal.

5. The system of claim 1 in which the information includes a command from the glucose measuring device to at least partially control the continuous glucose sensor.

6. The system of claim 5 in which the command from said glucose measuring device is to automatically activate processing of the information by said continuous glucose sensor based on transmitting the blood glucose value to said continuous glucose sensor.

7. The system of claim 1 in which said continuous glucose sensor is configured to send data to said glucose measuring device during the defined time span, and said glucose measuring device is configured to process the data received from said continuous glucose sensor.

8. The system of claim 7 in which said glucose measuring device is configured to process the data during the defined time span.

9. A method of communicating between a glucose measuring device and a continuous glucose sensor, the glucose measuring device including a communication module configured to activate from a deactivated state a wireless communication link enabling communication between the glucose measuring device and the continuous glucose sensor, comprising:

transmitting from the continuous glucose sensor to the glucose measuring device a first physiological parameter representative of the glucose value of an animal;

using the first physiological parameter, determining a defined time span for the wireless communication link to be established;

using the glucose measuring device, generating a blood glucose value based upon a second physiological parameter representative of the blood glucose concentration of the animal;

in response to the completion of the generation of the blood glucose value, automatically activating the communication link for the defined time span;

during the predetermined defined time span, transmitting information from the glucose measuring device to the continuous glucose sensor;

processing the information using the continuous glucose sensor; and upon expiration of the defined time span, automatically deactivating the communication link.

10. The method of claim 9 in which said processing comprises the continuous glucose sensor processing the information during the defined time span.

11. The method of claim 9 in which said deactivating comprises the communication module deactivating the wireless link between the glucose measuring device and the continuous glucose sensor upon expiration of the defined time span.

12. The method of claim 9 in which the information includes a command from the glucose measuring device to at least partially control the continuous glucose sensor.

13. The method of claim 12 in which the command from the glucose measuring device is to automatically activate processing of the information by the continuous glucose sensor based on transmitting the blood glucose value to the continuous glucose sensor.

14. The method of claim 9 and further including sending data from the continuous glucose sensor to the glucose measuring device during the defined time span and processing the data using the glucose measuring device.

15. The method of claim 14 in which said processing the data comprises the glucose measuring device processing the data during the defined time span.

\* \* \* \* \*